United States Patent [19]

Shehata

[11] Patent Number: 5,445,874
[45] Date of Patent: Aug. 29, 1995

[54] WATERPROOF, BLOOD-PROOF AND VIRUS-PROOF BREATHABLE LAMINATES

[75] Inventor: Hussein A. Shehata, Lawrenceville, N.J.

[73] Assignee: Fabrite Scientific Corp., Wood-Ridge, N.J.

[21] Appl. No.: 59,916

[22] Filed: May 10, 1993

[51] Int. Cl.⁶ .............................. B32B 7/00
[52] U.S. Cl. ................... 428/252; 428/246; 428/253; 428/284; 428/287
[58] Field of Search .............. 428/252, 253, 260, 265, 428/267, 287, 290, 246, 284

[56] References Cited

U.S. PATENT DOCUMENTS 4,908,260  3/1990  Dodia et al. ................. 428/215

*Primary Examiner*—James J. Bell
*Attorney, Agent, or Firm*—Mathews, Woodbridge & Collins

[57] ABSTRACT

The present relates to laminates which are waterproof blood-proof and virus-proof with a very high moisture vapor transmission rate. The laminate includes a woven or non-woven fabric and an extruded film of 60–70% butylene terephthalate units and the balance a polyester glycol.

5 Claims, No Drawings

WATERPROOF, BLOOD-PROOF AND VIRUS-PROOF BREATHABLE LAMINATES

BACKGROUND OF THE INVENTION

The present invention pertains to laminates which are waterproof, blood-proof and virus-proof, yet have a very high moisture vapor transmission. These laminates are suitable for use in protective apparel for adverse climate conditions (i.e. rainwear, skiwear and the like) as well as for hospital or medical garments which must withstand adverse washing and sterilization conditions.

Recent studies have shown the risk to healthcare workers of viral disease transmission from infected patients to be extremely high. In 234 operations ranging from general to cardiothoracic surgery and including six other surgical specialties, 50 percent resulted in at least one person becoming contaminated. Routes of contamination were through cuts, sticks and splashes.

The Occupational Safety & Health Administration's (OSHA) final regulation regarding occupational exposure to bloodborne pathogens appeared in the Federal Register on Dec. 6, 1991. This final regulation is extremely far reaching in its attempt to offer healthcare workers a realistic approach in addressing means for minimizing risk in the present environment, in which the threat of both Human Immunodeficiency Virus (HIV) and Hepatitis B Virus (HBV) exposure are of great concern. The regulation requires that gowns and fabrics which are now available must offer sufficient resistance to fluid penetration and virus penetration and must be washable and sterilizable a minimum of 100 times at 275 degrees Fahrenheit for 5 minutes to reduce the cost of health care.

Any employee who may be exposed to human bodily fluids which may be infectious is covered by the OSHA regulation. Thus the entire healthcare sector is covered by the OSHA standard, including hospitals, outpatient facilities, medical and dental laboratories, physician's offices, nursing homes, research laboratories, linen services, and handlers of regulated waste. Outside the healthcare community, the regulation also covers the areas of law enforcement, fire and rescue organizations and correctional institutions. A total of 5.6 million workers are estimated to be covered by this regulation, 78 percent of which are employed in the healthcare profession.

Currently, the most commonly used waterproof, but breathable, laminated fabric is Gore-tex II ® produced by W. L. Gore Associates Inc. A microporous poly-tetrafluoroethylene (PTFE) laminate material is riddled with billions of tiny pores too small for water droplets to penetrate, but large enough for water vapor to escape. This microporous PTFE is laminated to the inside of a wide variety of fabrics. To achieve a lamination without interfering with breathability, millions of tiny dots of adhesive are used to laminate the PTFE membrane onto fabric (since the PTFE membrane cannot be successfully laminated directly onto the fabric). U.S. Pat. No. 4,194,041 to Gore et al. discloses using at least one layer of a hydrophilic material, such as Hypol ® (by W. R. Grace & Co.) to coat the PTFE membrane to prevent the transport of surface active agents and contaminating substances, such as those found in perspiration, detergent and soap, and to prevent abrasion, which can affect the ability of the PTFE membrane to prevent water penetration.

This fabric has several drawbacks, including its cost. The PTFE membrane has no elastic recovery. In addition, the PTFE membrane is sensitive to scratching (hence its use as a "sandwich" laminate or as an insert in high performance garments). Finally, such microporous membranes are often less effective than desired as they have too many oversized pores.

SUMMARY OF THE INVENTION

The present invention relates to laminates comprising (i) a woven or non-woven fabric and (ii) an extruded film of 60-70% butylene terephthalate units and the balance a polyether glycol.

The present invention also relates to laminates comprising (i) a woven or non-woven fabric and (ii) an extruded film of 60-70% butylene terephthalate units and the balance a polyether glycol, the film being laminated to the fabric with a polyester- or polyether-polyurethane adhesive which has been pre-treated with an epoxy or carbodiimide.

The laminates of the present invention have a solid film that prevents viruses, blood, water, and other liquids from penetrating the fabric and reaching the skin, while allowing high moisture vapor transmission (MVT) from the skin surface out for the comfort of the wearer. Since these are solid film laminates, there are no pores which can be affected by perspiration, detergents and soaps, which can cause microporous membranes to leak. Finally, the laminates yield a reusable and rewashable material than can stand at least 100 washes and can be autoclaved at 275 degrees Fahrenheit for 5 minutes. As such, the laminates of the present invention provide an excellent and superior substitute to Gore-tex II ®.

The laminates of the present invention are suited for any clothing or apparel where it is desirable or necessary to prevent liquids from penetrating through to the wearer's skin. Uses for these laminates include rainwear, skiwear, sports garments, hospital gowns and other medical garments, and government uniforms. Due to the stretchability of the laminates and 100 percent recovery, they are particularly suited for protective gloves and socks.

DESCRIPTION OF THE PREFERRED EMBODIMENTS

The preferred film for use in the present invention contains polymer polyester elastomers which are all block copolymers consisting of 60-70% of a hard (crystalline) segment of polybutylene terephthalate and the balance a soft (amorphous) segment based on long chain polyether glycols. While the soft segments are preferably based on long chain polyethylene glycols, comparable long chain polyether glycols, such as long chain polypropylene glycols, also are suitable.

A commercially available material which would provide a suitable film is Hytrel ®, a thermoplastic elastomer from DuPont. Hytrel ® is a hard segment of diol terephthalate and a soft segment of polyether diol terephthalate. Particularly suitable for the present invention is a mixture of Hytrel ® HTR 8206 and Hytrel ® HTR 8171, which provides a film with high MVT. Hytrel ® HTR8206 has a flexural modulus tested by ASTM D790 of 80 MPa and a nominal durometer hardness of 45D. HTR 8206 has a crystalline melting point of 200° C. and is completely melted at 223° C. HTR8206 has a specific gravity tested by ASTM 8792 of 1.19. A one mil extruded film of either Hytrel ® HTR8206 or Hytrel ® HTR8171 alone, or a mixture of both in ratio of from about 70–80 to about 20–30 will have a MVT rate of from 10,000 to 15,000 g/m$^2$/day measured with ASTM E-96-BW.

Other examples of suitable polymer materials which are hydrophilic in nature and can be formulated to produce a solid film with high MVT (i.e. MVT rate of at least 6,000 g/m$^2$/day measured with ASTM E-96-B).

The solid films used in the laminate of the present invention are vapor permeable due to hydrophilic chemistry. The solid film consists of carbon, hydrogen and oxygen atoms linked together in long molecular chains. Positive and negative charges arise at different points, enabling the atoms to make weak bonds with the small water vapor molecules which stay bonded until they are displaced by other water vapor molecules, causing all of the water vapor molecules to travel through the film at lightning speed. The vapor pressure differential drives the water vapor molecules on the body side having the higher vapor pressure (higher moisture content) outward to the side having the lower vapor pressure as the system moves toward equilibrium.

Other additive compounds may be added to the polymer material used to produce the film which can enhance either processability, durability and/or wearability characteristics. Examples of such additives include antiblock concentrate color-stable antioxidants. HTREI® 20 UV can be used for protective against UV degradation and HYTREC® HS can be used to retard. Thermal oxidative degradation and extend useful life elevated temperatures. The polymer materials used in the present invention can be melted, typically at a temperature between 433 and 455 degrees Fahrenheit, and then extruded directly onto fabric or as a coating onto release paper. Alternatively, the polymer material can be extruded as a blown film. The solid film typically is from about 0.75 to about 3 mil in thickness.

The woven or non-woven fabric of the present laminate can be any fabric which is suitable for use in protective garments for the outdoors (e.g. rainwear, skiwear) or a medical setting. Examples of suitable fabrics currently used in such garments are polyester, nylon, polypropylene, Dupont Sontara®, tricot knit cloth nylon or brushed polyester.

The protective, breathable film can be laminated onto fabric by any conventional method for laminating films onto fabrics. The method should be one which will provide the desired softness, washability, permeability and drape of the laminate. Examples of suitable methods include powder lamination, hot melt lamination, and wet adhesive lamination.

In powder lamination, the adhesive is powder form. The most commonly used adhesive in powder lamination is a polyester adhesive and polyamide. The resultant bonded laminate is soft and washable. The polyester adhesives have melting points ranging from 100 to 130 degrees Fahrenheit. Other adhesives can have different melting points.

In a dry powder laminating line or machine, the adhesive is applied by a dry powder distribution device, such as a scatter coating applicator or spray nozzle, to form a web. The web then is conveyed on a heated belt through an infrared oven to melt the adhesive. The length of heater section, type, and watt density of the heaters, heater height, the conveyor belt temperature, and line speed all determine the temperature the adhesive reaches. The adhesive—an activated web—is then passed through temperature controlled nip rolls. At this point the web is compressed to maximize the number of point bonds. The nip roll pressure also marries the two substrates, in this case, the substrate and the film.

In hot melt lamination, the adhesive is melted before it is applied on the fabric with a spray nozzle. The processing then basically is as outlined above for powder lamination.

In the wet adhesive lamination method, the adhesive coating is applied with a coating head, usually a gravure type. The gravure roller is engraved. There are several precision engraving types, such as pyramid quad, trihelical, and hexagon. The depth of the engraving cell will control the amount the adhesive deposited on the fabric. This kind of adhesive printing will maintain the MVT of the film. After the film and fabric layers are in place, the curing of the adhesive will depend on the type of adhesive and the percent of solid in the adhesive.

In the wet adhesive lamination method, a two-part system of a polyurethane (isocyanate) adhesive with either a polyester or a polyether is more washable than the polyurethane adhesive alone, but it will still not meet the standard of 100 washes and ability to autoclave. As this invention intends to provide a more durable laminate, the above two-part polyester- or polyether-polyurethane adhesive system must be mixed with either a carbodiimide or an epoxy. A preferred weight ratio for such three-part adhesive systems is 6:2:1 (polyester or polyether:carbodiimide or epoxy:polyurethane).

Suitable carbodiimides include aromatic carbodites such as Staboxol I® (Bayer), which is 2,2',6,6'-tetraisopropyldiphenyl carbodiimide having a molecular weight of 362. Such compounds will improve the hydrolytic stability of the polyester-polyurethane adhesives.

For polyether-polyurethane adhesives, self-emulsifying epoxy resin or other compounds of the same chemical nature will enhance stability. A laminated material using this three-part adhesive system will cure within a few hours, and further heat curing at 300 degrees Fahrenheit will complete the chemical reaction. The final result is a three layer laminate which, when washed and autoclaved 100 times, does not show any delamination.

The following examples will serve to further typify the nature of the invention but should not be construed as a limitation on the scope thereof, which is defined solely by the appended claims.

EXAMPLE 1

A laminate is produced as follows:

A plain weave nylon of 2.8+.02 oz/sq$^2$ was laminated to a water proof breathable film using a mixture of adhesive of soluble bond #173 and soluol bond #1101 in a ratio of 5:1 using a gravure engraved roller. The amount of adhesive used was 0.5 to 0.8 oz/yd$^2$. The fabric was cured at 300° F. The fabric was laminated to a tricot knitcloth nylon with the same adhesive in an amount of 1.5 oz/yd$^2$ and was cured at 300° F.

The laminate so produced is found to have:

| | |
|---|---|
| Moisture Vapor Transmission Rate (g/mil/m$^2$/day) (ASTM E-96-B) | 800–950 |
| Procedure (g/m$^2$/day) (ASTM E-96-BW) | 6000–9000 |
| Hydrostatic Resistance (P.S.I.) (ASTM-5512) | 160 P.S.I. |
| Hydrostatic Resistance After Stretching of Coating | 140 P.S.I. |
| Hydrostatic Resistance After Insect Repellant | 140 P.S.I. |

| | |
|---|---|
| and Chemical Exposure | |
| Water Permeability | No Leakage |
| (ASTM-5516) for five minutes | at 50 cm |
| Resistance to Organic Liquid | No Leakage |
| Abrasion Resistance | No Damage |
| (Stoll - 10,000 cycle) | No Leakage |

The water permeability tests after flexing at 70 degrees Fahrenheit and after flexing at −25 degrees Fahrenheit (extreme cold weather) for 1500 cycles, show no leakage.

EXAMPLE 2

Hydrostatic Resistance Test (ASTM-5512)

This test is used to determine the resistance of laminated cloth to the passage of water under high pressure. While a minimum of 25 P.S.I. is required, 50 P.S.I. is the minimum needed for waterproof/breathable membranes.

Water pressure is applied to the face side of the laminate from Example(s) 1. The hydrostatic resistance is determined to be 146 P.S.I.

EXAMPLE 3

ASTM-F 903 Challenge (Synthetic Blood)

Protocol for Microbiological Barrier Testing of Protective Clothing Materials Used to Protect Against Bloodborne Pathogens Three ply fabric is laminated using a different woven material weight from 2 oz/yd to 8 oz/yd or knit, and a fabric polyester weight from 1.2 oz/yd to 6 oz/yd. This fabric is challenged with synthetic blood for five minutes at atmospheric pressure, one minute at 2 P.S.I. and 54 minutes at atmospheric pressure. This fabric passes all blood challenges.

EXAMPLE 4

F 903 QX 174 Challenge Test

A laminate was prepared using 100% brushed polyester fabric of 3.8 oz/yd$^2$ laminated with soluol bond poly ether #63–100 and solual bond polyester 1101 and apoxy resin in a ratio of 5:1:1 to a water proof breathable film using an engraved gravure roller. The fabric was cured at 280° F. The fabric was laminated to brushed polyester fabric of 2.8 oz/yd$^2$ with the same adhesive and cured at 280° F.

Standard Test Procedure for Virus Penetration Adapted from the NFPA 1992 "Standard on Liquid Splash Protective Suits for Hazardous Chemical Emergencies" and in Accordance with ASTM Draft F.22.70.02 Procedure was used on the laminate.

The laminate using the film of the present invention is challenged with a liter of $2.00 \times 10^8$ PFU/ml and found to be completely protective against virus transmission.

EXAMPLE 5

Laundering

The laminated material of Example 4 is tested for endurance in the hospital laundering process, which uses strong detergents, bleach, alkaline and acid solutions, high temperatures in both washing and drying, and autoclaving to eliminate harmful microbes. After 100 times, the laminate is found to be satisfactory.

EXAMPLE 6

Standard Test Method for Water Vapor Transmission (ASTM E-906-80)

Using the laminate from Example 1 as the test specimen, the test vessel is filled with water up to ¾ to ½ inches from where the specimen is to be placed to avoid having the water touch the specimen. The specimen is attached to the disk assembly, and the disk assembly is weighed before being set in place. After 24 hours the disk assembly is again weighed and the MVT is found to be 870 g/m$^2$/day measured with ASTM E-96-B.

What is claimed is:

1. A protective laminate comprising (i) a woven or non-woven fabric and (ii) an extruded film of a hard segment of from 60 to 70% butylene terephthalate units and the balance a soft segment of polyetherdiol terephthalate, a first layer of said fabric and a second layer of said fabric said film being laminated between said first and second layers of fabric.

2. A protective laminate comprising (i) a woven or non-woven fabric and (ii) a hard segment of an extruded film of 60–70% butylene terephthalate units and the balance a soft segment of polyetherdiol terephthalate, the film being laminated to the fabric with a polyester- or polyether-polyurethane adhesive which has been pre-treated with an epoxy or carbodiimide wherein said adhesive has a ratio of polyester or polyether to carbodiimide or epoxy to polyurethane of 6:2:1.

3. The laminate of claim 2 wherein said carbodiimide is 2,2',6,6' tetraisopropyldiphenyl carbodiimide.

4. The laminate of claim 2 wherein said film has a moisture vapor transmission rate of at least 600 g/m$^2$/day.

5. The laminate of claim 2 wherein said fabric is selected from the group comprising polyester, nylon, tricot knit nylon, brushed polyester, and polypropylene.

* * * * *